US012668124B2

(12) United States Patent
Ljungblad et al.

(10) Patent No.: US 12,668,124 B2
(45) Date of Patent: Jun. 30, 2026

(54) SENSOR SYSTEM FOR PASSIVE IN-VEHICLE BREATH ALCOHOL ESTIMATION

(71) Applicant: Automotive Coalition for Traffic Safety, Inc., Sterling, VA (US)

(72) Inventors: Jonas Ljungblad, Stockholm (SE); Magnus Öberg, Sterling, VA (US)

(73) Assignee: Automotive Coalition for Traffic Safety, Inc., Ashburn, VA (US)

( * ) Notice: Subject to any disclaimer, the term of this patent is extended or adjusted under 35 U.S.C. 154(b) by 0 days.

(21) Appl. No.: 18/643,488

(22) Filed: Apr. 23, 2024

(65) Prior Publication Data

US 2025/0091435 A1    Mar. 20, 2025

Related U.S. Application Data

(63) Continuation-in-part of application No. 17/462,318, filed on Aug. 31, 2021, now Pat. No. 11,964,558, (Continued)

(51) Int. Cl.
*G06F 17/00* (2019.01)
*B60K 28/06* (2006.01)
(Continued)

(52) U.S. Cl.
CPC ....... *B60K 28/063* (2013.01); *G01N 33/0067* (2013.01); *G01N 33/4972* (2013.01)

(58) Field of Classification Search
CPC ............. B60K 28/063; G01N 33/0067; G01N 33/4972
(Continued)

(56) References Cited

U.S. PATENT DOCUMENTS 3,283,563 A    11/1966    Turner et al.
3,301,482 A    1/1967    Bullen
(Continued)

FOREIGN PATENT DOCUMENTS

CN    1586944    3/2005
CN    101292158    10/2008
(Continued)

OTHER PUBLICATIONS

Highly accurate breath test system (Year: 2013).*
(Continued)

*Primary Examiner* — Ronnie M Mancho
(74) *Attorney, Agent, or Firm* — Pandiscio & Pandiscio

(57) ABSTRACT

A method for passive breath alcohol detection, the method comprising: A) passively obtaining a first air sample from the air inside the interior of a vehicle; B) determining the concentration of (i) a tracer gas, and (ii) an analyte present in the first air sample; C) passively obtaining a second air sample from the air inside the interior of the vehicle; D) determining the concentration of (i) the tracer gas, and (ii) the analyte present in the second air sample; E) continuing to passively obtain an N number of air samples from the air inside the interior of the vehicle, and for each air sample obtained, determining the concentration of the tracer gas and the analyte present in the air sample; F) determining a number of peaks in the concentration of the tracer gas and a number of peaks in the concentration of the analyte present in each of the air samples; G) determining a confidence interval based on the number of peaks in the concentration of the tracer gas and the number of peaks in the concentration of the analyte; and H) controlling operation of the vehicle based on a function of the confidence interval and the concentration of the analyte present in the air samples.

25 Claims, 8 Drawing Sheets

Related U.S. Application Data which is a continuation of application No. 15/389,724, filed on Dec. 23, 2016, now Pat. No. 11,104,227.

(60) Provisional application No. 63/562,889, filed on Mar. 8, 2024, provisional application No. 62/312,476, filed on Mar. 24, 2016.

(51) Int. Cl.
    *G01N 33/00*         (2006.01)
    *G01N 33/497*      (2006.01)

(58) Field of Classification Search
    USPC ............................................................. 701/1
    See application file for complete search history.

(56)           References Cited

U.S. PATENT DOCUMENTS

| | | | |
|---|---|---|---|
| 3,780,311 A | 12/1973 | Brown | |
| 3,792,272 A | 2/1974 | Harte et al. | |
| 3,792,351 A | 2/1974 | Ireland | |
| 3,830,630 A | 8/1974 | Kiefer et al. | |
| 3,897,659 A | 8/1975 | Henry | |
| 4,090,078 A | 5/1978 | Heim | |
| 4,294,327 A | 10/1981 | Howard | |
| 4,535,620 A | 8/1985 | Cunningham | |
| 4,678,057 A | 7/1987 | Elfman et al. | |
| 4,749,553 A | 6/1988 | Lopez et al. | |
| 4,843,377 A | 6/1989 | Fuller et al. | |
| 4,868,545 A | 9/1989 | Jones | |
| 4,916,435 A | 4/1990 | Fuller | |
| 4,975,581 A | 12/1990 | Robinson et al. | |
| 4,996,161 A | 2/1991 | Conners et al. | |
| 5,006,315 A | 4/1991 | Maroulis et al. | |
| 5,303,575 A | 4/1994 | Brown et al. | |
| 5,426,415 A | 6/1995 | Prachar et al. | |
| 5,458,853 A | 10/1995 | Porter et al. | |
| 5,485,850 A | 1/1996 | Dietz | |
| 5,544,276 A | 8/1996 | Loux et al. | |
| 5,652,398 A | 7/1997 | Johnson | |
| 5,655,530 A | 8/1997 | Messerschmidt | |
| 5,693,944 A | 12/1997 | Rich | |
| 5,746,973 A | 5/1998 | Naraqhi | |
| 5,823,951 A | 10/1998 | Messerschmidt | |
| 5,830,112 A | 11/1998 | Wanq et al. | |
| 5,877,345 A | 3/1999 | Bauer et al. | |
| 5,906,203 A | 5/1999 | Klockseth et al. | |
| 5,955,886 A | 9/1999 | Cohen et al. | |
| 5,971,937 A | 10/1999 | Ekstrom | |
| 6,123,674 A | 9/2000 | Rich | |
| 6,129,680 A | 10/2000 | Mottram | |
| 6,142,951 A | 11/2000 | Park | |
| 6,152,876 A | 11/2000 | Robinson et al. | |
| 6,157,041 A | 12/2000 | Thomas et al. | |
| 6,229,908 B1 | 5/2001 | Edmonds et al. | |
| 6,266,353 B1 | 7/2001 | Freitas et al. | |
| 6,441,388 B1 | 8/2002 | Thomas et al. | |
| 6,468,222 B1 | 10/2002 | Mault et al. | |
| 6,488,635 B1 | 12/2002 | Mottram | |
| 6,528,809 B1 | 3/2003 | Thomas et al. | |
| 6,608,399 B2 | 8/2003 | McConnell et al. | |
| 6,622,032 B1 | 9/2003 | Robinson et al. | |
| 6,684,099 B2 | 1/2004 | Ridder et al. | |
| 6,726,636 B2 | 4/2004 | Der Ghazarian et al. | |
| 6,748,301 B1 | 6/2004 | Ryu | |
| 6,794,988 B1 | 9/2004 | Weiss et al. | |
| 6,862,091 B2 | 3/2005 | Johnson | |
| 6,983,176 B2 | 1/2006 | Gardner et al. | |
| 7,016,713 B2 | 3/2006 | Gardner et al. | |
| 7,092,832 B2 | 8/2006 | Brown | |
| 7,098,037 B2 | 8/2006 | Haas et al. | |
| 7,173,524 B2 | 2/2007 | Ponziani | |
| 7,202,091 B2 | 4/2007 | Jones et al. | |
| 7,386,152 B2 | 6/2008 | Rowe et al. | |
| 7,446,878 B2 | 11/2008 | Ridder et al. | |
| 7,671,752 B2 | 3/2010 | Sofer | |
| 7,736,903 B2 | 6/2010 | Lambert et al. | |
| 7,764,982 B2 | 7/2010 | Dalke et al. | |
| 7,848,605 B2 | 12/2010 | Ridder et al. | |
| 7,993,281 B2 | 8/2011 | Stock et al. | |
| 8,306,595 B2 | 11/2012 | Osaki et al. | |
| 8,469,134 B2 | 6/2013 | Osaki et al. | |
| 8,605,959 B2 | 12/2013 | Kangas | |
| 8,773,390 B1 | 7/2014 | Clark | |
| 9,068,885 B2 | 6/2015 | Kluczynski et al. | |
| 9,073,431 B2 | 7/2015 | Takahashi | |
| 9,163,718 B2 | 10/2015 | Nelson | |
| 9,823,237 B2 * | 11/2017 | Martin | G01N 33/4972 |
| 10,151,744 B2 | 12/2018 | Hok et al. | |
| 11,104,227 B2 * | 8/2021 | Hök | B60K 28/063 |
| 11,391,724 B2 * | 7/2022 | Hok | A61B 5/0059 |
| 2002/0084130 A1 | 7/2002 | Der Ghazarian et al. | |
| 2002/0140289 A1 | 10/2002 | McConnell et al. | |
| 2003/0039299 A1 | 2/2003 | Horovitz | |
| 2003/0048000 A1 | 3/2003 | Harter | |
| 2003/0085284 A1 | 5/2003 | Bremer et al. | |
| 2004/0093957 A1 | 5/2004 | Buess et al. | |
| 2004/0260194 A1 | 12/2004 | Baver | |
| 2005/0241871 A1 | 11/2005 | Stewart et al. | |
| 2006/0058697 A1 | 3/2006 | Mochizuki et al. | |
| 2006/0153740 A1 * | 7/2006 | Sultan | G01N 21/3504 |
| | | | 422/88 |
| 2006/0154377 A1 * | 7/2006 | Lambert | G01N 21/05 |
| | | | 436/167 |
| 2006/0167349 A1 | 7/2006 | Gardner et al. | |
| 2006/0206034 A1 | 9/2006 | Stock et al. | |
| 2006/0210120 A1 | 9/2006 | Rowe et al. | |
| 2006/0253711 A1 | 11/2006 | Kallmann | |
| 2007/0077176 A1 | 4/2007 | Lambert et al. | |
| 2007/0142720 A1 | 6/2007 | Ridder et al. | |
| 2007/0144812 A1 | 6/2007 | Stewart et al. | |
| 2007/0245801 A1 | 10/2007 | Stock | |
| 2008/0006077 A1 | 1/2008 | Crabtree et al. | |
| 2008/0045806 A1 | 2/2008 | Keppler | |
| 2008/0061238 A1 | 3/2008 | Hok et al. | |
| 2008/0107309 A1 | 5/2008 | Carni | |
| 2008/0171947 A1 | 7/2008 | Ruffert | |
| 2008/0228098 A1 | 9/2008 | Popov et al. | |
| 2008/0252412 A1 | 10/2008 | Larsson et al. | |
| 2008/0319286 A1 | 12/2008 | Ridder et al. | |
| 2009/0007634 A1 | 1/2009 | Mitchell | |
| 2009/0039267 A1 | 2/2009 | Arndt et al. | |
| 2009/0087920 A1 | 4/2009 | Pettersson et al. | |
| 2009/0248260 A1 | 10/2009 | Flanagan | |
| 2009/0293589 A1 | 12/2009 | Freund et al. | |
| 2010/0010325 A1 | 1/2010 | Ridder et al. | |
| 2010/0028210 A1 | 2/2010 | Ozaki et al. | |
| 2010/0031718 A1 | 2/2010 | Heil | |
| 2010/0036592 A1 | 2/2010 | Osaki et al. | |
| 2010/0063409 A1 | 3/2010 | Hok | |
| 2010/0188232 A1 | 7/2010 | Lambert et al. | |
| 2010/0268425 A1 | 10/2010 | Pettersson et al. | |
| 2010/0327167 A1 | 12/2010 | Koop et al. | |
| 2011/0178420 A1 | 7/2011 | Ridder et al. | |
| 2011/0283770 A1 | 11/2011 | Hok | |
| 2011/0302992 A1 | 12/2011 | Robbins et al. | |
| 2011/0308297 A1 | 12/2011 | Tsuzuki et al. | |
| 2011/0309932 A1 | 12/2011 | Arrinqdale et al. | |
| 2012/0112879 A1 | 5/2012 | Ekchian et al. | |
| 2013/0110311 A1 | 5/2013 | Ver Steeg | |
| 2013/0231871 A1 | 9/2013 | Hok | |
| 2014/0002237 A1 | 1/2014 | Infante et al. | |
| 2014/0156149 A1 | 6/2014 | Feit | |
| 2014/0260537 A1 | 9/2014 | Nash | |
| 2014/0297061 A1 | 10/2014 | Takahashi | |
| 2014/0318293 A1 | 10/2014 | Nelson | |
| 2014/0377877 A1 | 12/2014 | Bürgi et al. | |
| 2015/0066238 A1 | 3/2015 | Todd et al. | |
| 2015/0219620 A1 | 8/2015 | Hök et al. | |
| 2015/0233897 A1 | 8/2015 | Hök | |
| 2016/0356764 A1 | 12/2016 | Martin et al. | |
| 2017/0050518 A1 | 2/2017 | Steeg et al. | |
| 2017/0074857 A1 * | 3/2017 | Dennis | A61B 5/4848 |
| 2017/0274768 A1 * | 9/2017 | Hök | G01N 33/4972 |

(56) References Cited

U.S. PATENT DOCUMENTS

| | | | | |
|---|---|---|---|---|
| 2022/0242416 A1* | 8/2022 | Ljungblad | .......... | B60H 1/00742 |
| 2023/0041464 A1* | 2/2023 | Jung | .................. | B60K 28/066 |
| 2025/0091435 A1* | 3/2025 | Ljungblad | .......... | G01N 33/4972 |

FOREIGN PATENT DOCUMENTS

| | | | | |
|---|---|---|---|---|
| CN | 101334399 A | 12/2008 | | |
| CN | 101624015 | 1/2010 | | |
| CN | 101631497 | 1/2010 | | |
| CN | 102316801 A | 1/2012 | | |
| CN | 102854303 | 1/2013 | | |
| CN | 104816692 | 8/2015 | | |
| DE | 4127599 A1 | 2/1993 | | |
| DE | 198 11 872 | 8/1999 | | |
| DE | 199 38 064 | 8/2000 | | |
| DE | 101 57 907 | 6/2003 | | |
| DE | 102006018970 B3 | 5/2007 | | |
| DE | 102011106410 | 8/2012 | | |
| EP | 0752584 | 1/1997 | | |
| EP | 0791899 | 8/1997 | | |
| EP | 1154224 A1 * | 11/2001 | ......... | G01B 9/02003 |
| EP | 1441212 | 7/2004 | | |
| EP | 1688741 | 8/2006 | | |
| EP | 3304045 | 4/2008 | | |
| EP | 3433611 | 1/2019 | | |
| GB | 2431470 | 4/2007 | | |
| GB | 2442980 | 4/2008 | | |
| JP | 11-104112 | 4/1999 | | |
| JP | 2004-245799 | 9/2004 | | |
| JP | 2004-305494 | 11/2004 | | |
| JP | 2005-157599 | 6/2005 | | |
| JP | 2006-98058 | 4/2006 | | |
| JP | 2007-147592 | 6/2007 | | |
| JP | 2008-253455 | 10/2008 | | |
| JP | 2008-291710 | 12/2008 | | |
| JP | 2008-302915 | 12/2008 | | |
| JP | 2008-308037 | 12/2008 | | |
| JP | 2009-217633 | 9/2009 | | |
| JP | 2009-257768 | 11/2009 | | |
| JP | 2010-139319 | 6/2010 | | |
| JP | 2010-241369 | 10/2010 | | |
| JP | 2011-153956 | 8/2011 | | |
| JP | 2012-198648 | 10/2012 | | |
| JP | 2016-538193 | 12/2016 | | |
| KR | 20080110567 | 12/2008 | | |
| SE | 536782 | 8/2014 | | |
| SE | 536784 | 8/2014 | | |
| WO | WO 92/22813 | 12/1992 | | |
| WO | WO 95/26889 | 10/1995 | | |
| WO | WO 97/000443 | 1/1997 | | |
| WO | WO 98/20346 | 5/1998 | | |
| WO | WO 2001/008554 | 2/2001 | | |
| WO | WO 2004/090786 | 10/2004 | | |
| WO | WO 2007/046745 | 4/2007 | | |
| WO | WO 2008/108714 | 9/2008 | | |
| WO | WO 2009/048809 | 4/2009 | | |
| WO | WO 2010/085716 | 7/2010 | | |
| WO | wo 2010/093317 | 8/2010 | | |
| WO | WO 2012/064252 | 5/2012 | | |
| WO | WO 2013/081519 | 6/2013 | | |
| WO | WO 2014/031071 | 2/2014 | | |
| WO | WO 2014/031072 | 2/2014 | | |
| WO | WO 2016/195803 | 12/2016 | | |
| WO | WO 2017/164953 | 9/2017 | | |

OTHER PUBLICATIONS

Highly accurate breath test system (Year: 2013) (Year: 2013).*

Blincoe, L. J. et al., The Economic and Societal Impact Of Motor Vehicle Crashes, 2010 (Revised), National Highway Traffic Safety Administration, May 2015 (Revised), DOT HS 812 013.

Dhokalia et al., Resting End-Tidal $CO_2$ Association With Age, Gender, and Personailty, Psychosomatic Medicine, vol. 60, 1998, pp. 33-37.

Extended European Search Report EP 13 83 0956 dated Jul. 13, 2015.

Extended European Search Report EP 13 83 1692 dated Jul. 13, 2015.

Giebel, Brian M., Thesis and Dissertation, "Advancement and Application of Gas Chromatography Isotope Ratio Mass Spectrometry Techniques for Atmospheric Trace Gas Analysis," Published 2011, 252 total pages.

International Search Report dated Feb. 3, 2014 for PCT/SE2013/050991.

International Search Report dated Jan. 31, 2014 for PCT/SE2013/050990.

Lambert et al., Passive Sensing of Driver Intoxication, SAE Technical Paper 2006-01-1321, 2006, SAE International.

Ljungblad, J. et al., Development and Evaluation of Algorithms for Breath Alcohol Screening, Sensors, Apr. 2016, vol. 16, No. 469, pp. 1-7.

Talbert, Bruce, et al., "A Study of Regulators for Delivering Gases Containing Low Concentrations of Hydrogen Sulfide," LCGC North America, 22(6):562, 564, 567-568 (2004).

Traffic Safety Facts, 2013 Data: Alcohol-Impaired Driving, National Highway Traffic Safety Administration, Dec. 2014, DOT HS 812 102.

* cited by examiner

112

114

SENSOR SYSTEM FOR PASSIVE IN-VEHICLE BREATH ALCOHOL ESTIMATION

REFERENCE TO PENDING PRIOR PATENT APPLICATIONS

This patent application:

(i) is a continuation-in-part of pending prior U.S. patent application Ser. No. 17/462,318, filed Aug. 31, 2021 for SENSOR SYSTEM FOR PASSIVE IN-VEHICLE BREATH ALCOHOL ESTIMATION by Automotive Coalition for Traffic Safety, Inc., which patent application, in turn:

(a) is a continuation of prior U.S. patent application Ser. No. 15/389,724, filed Dec. 23, 2016 for SENSOR SYSTEM FOR PASSIVE IN-VEHICLE BREATH ALCOHOL ESTIMATION by Automotive Coalition for Traffic Safety, Inc., which patent application, in turn:

(1) claims benefit of prior U.S. Provisional Patent Application Ser. No. 62/312,476, filed Mar. 24, 2016 for SENSOR SYSTEM FOR PASSIVE IN-VEHICLE BREATH ALCOHOL ESTIMATION by Automotive Coalition for Traffic Safety, Inc.; and (ii) claims benefit of prior U.S. Provisional Patent Application Ser. No. 63/562,889, filed Mar. 8, 2024 for SENSOR SYSTEM FOR PASSIVE IN-VEHICLE BREATH ALCOHOL ESTIMATION by Automotive Coalition for Traffic Safety, Inc.

The four (4) above-identified patent applications are hereby incorporated herein by reference.

FIELD OF THE INVENTION

This invention relates to methods for detection of breath alcohol concentrations in the exhaled breath of a driver, and more particularly to rapid estimations of a driver's breath alcohol level.

BACKGROUND OF THE INVENTION

Supervised breath tests are regularly performed by police in an effort to prevent drunk driving.

In addition to supervised breath tests, automated ignition interlock devices (sometimes called "alcolocks") that conduct unsupervised tests to prevent the operation of vehicles by drunk drivers, have been installed within vehicles themselves. Sensing technologies used for such breath tests may be based on catalytic beads (or pellistors), semiconductors, fuel cells or infrared spectroscopy. Fuel cells are the dominant sensing elements used for breath analyzers and alcolocks comprising a mouthpiece. Evidential instruments typically use infrared spectroscopy. Catalytic beads, pellistors, etc. are typically used in low cost devices for the consumer market and generally do not meet requirements on analytical specificity. Typical breath test devices provide a signal representing Breath Alcohol Concentration (BrAC) after a driver has taken a deep breath and emptied his or her airways into a mouthpiece, which for hygienic reasons is often a separate, disposable item. To ensure a correct determination, the test person is required to deliver a forced expiration approximating full vital capacity. This requires substantial time and effort, especially for people with limited capacity. More particularly, it should be appreciated that there is extremely wide variation in what is considered "full vital capacity" given a typical population. Certain passive breath tests performed in accordance with the present invention are possible without obtaining a forced expiration approximating full vital capacity for a given population (as would otherwise be necessary to perform an active breath test). It will be appreciated that the present invention generally utilizes a breath sample volume (e.g., 0.7-1.2 L) that is well below the full vital capacity of a typical adult.

Ease of use, convenience, and accuracy are important factors for increasing the acceptance and adoption of built-in ignition interlock devices in vehicles.

SUMMARY OF THE INVENTION

There is, therefore, a need for a passive breath test that is flexible enough to avoid inconvenience to the driver while ensuring accuracy of the test under a wide range of environmental conditions and driver behaviors. In a passive breath test, the driver need not provide directed air to the sensor, and the BrAC measurement will be made, without additional action of the driver, from the air within the vehicle, which will be a mixture of breath of both the driver and any passengers, as well as ambient air. In contrast, in an active breath test, the driver may be required to be close to the sensor, and to direct a forced, undiluted breath towards the sensor or through an air inlet (e.g., blowing into a tube). While a passive breath test is preferred, under some conditions it may not be possible to perform an accurate passive breath test. Such conditions may be environmental (e.g., very hot weather) or the result of driver attempts to defeat the system (some examples are described below), but either way may result in the air within the vehicle not accurately reflecting the driver's BrAC. If normal testing conditions, under which an accurate passive BrAC test is possible, are not met, then an active breath test is required.

A variety of parameters indicating both environmental conditions and driver behavior are measured to detect when normal testing conditions are no longer met. These include, for example, detecting a peak in a tracer gas concentration, which indicates that the driver's breath has been detected. A timer may set a time limit between when a driver's presence is detected and when a peak in the tracer gas concentration is detected. This time limit may prevent driver attempts to defeat the system by holding his or her breath, or otherwise concealing his or her breath from the sensor. A pressure sensor may detect situations in which a driver has attempted to defeat the system by ventilating the vehicle, or in which wind that is blowing through the vehicle may prevent an accurate passive breath test. Detecting the driver's head position relative to a sensor may ensure that the driver's breath is being directed towards the sensor, in order to prevent attempts to defeat the system by supply an alternate source of "breath" to be measured.

The methods and apparatus described herein allow for passive detection of breath alcohol concentration, and may be used for controlling ignition of a vehicle. In particular, the methods and apparatus are designed to determine BrAC from a passive breath test without inconveniencing the driver during normal testing conditions, detect when normal testing conditions no longer are met, and provide for BrAC measurement from an active breath test under those circumstances.

In an example of a method or apparatus for passive breath alcohol detection for operating a vehicle, the apparatus may include sensors which measure the concentration of a tracer gas in a passively obtained first air sample, while the method may include initiating the sensor system, passively obtaining a first air sample, and measuring the concentration of a tracer gas from the first air sample. The apparatus may include a processor, which determines, using the sensor system, a set of testing conditions based in part on the first air sample, while the method may include that determining. If the set of testing conditions is within a normal range and a peak in tracer gas concentration is detected, the method or processor measures a BrAC of a driver from the first air sample. If the set of testing conditions is outside of the normal range or no peak in tracer gas concentration is detected, the method or processor requests an active second air sample from the driver and measures the BrAC of the driver.

In some embodiments, the method includes measuring a time interval between initiating the sensor system and detecting the peak in tracer gas concentration. In some embodiments, the apparatus includes a timer which measures that time interval. If the time interval exceeds a predetermined time limit, the method or processor determines that the set of testing conditions is outside of the normal range. In some embodiments, the apparatus includes sensors which measure the environmental conditions of the vehicle, and in some embodiments the method includes measuring such environmental conditions. In some embodiments, such a sensor may be a temperature sensor, and in some embodiments the method includes measuring the temperature within the vehicle. If the temperature is outside a normal temperature range, the method or processor determines that the set of testing conditions is outside of the normal range. In some embodiments, the apparatus includes a pressure sensor to measure the pressure within the vehicle, and in some embodiments the method includes measuring that pressure. If the pressure is outside a normal pressure range, the method or processor determines that the set of testing conditions is outside of the normal range. In some embodiments, the apparatus includes a camera which measures the driver's head position relative to a BrAC sensor, and in some embodiments the method includes measuring the driver's head position relative to a BrAC sensor. In some embodiments, initiating the sensor system includes detecting the presence of the driver entering the vehicle. In some embodiments, measuring the BrAC of the driver from an active breath test includes determining if a measured BrAC from a passive breath test is at an intermediate level. If the measured BrAC is at the intermediate level, the method requests an active breath sample and measures BrAC. In some embodiments measuring the BrAC of the driver from an active breath test includes requesting, through a Human-Machine Interface (HMI), an undiluted breath sample directed towards the BrAC sensor.

In some embodiments, the method includes sending sensor signals to a central processing unit (CPU) of the breath test system, which is in communication with a CPU of the vehicle. In some embodiments, the processor receives the sensor signals from the sensors. In some embodiments, the method includes disabling the operation of the vehicle if the result of the driver's BrAC measurement is above a set point, which may also be done with a processor. In some embodiments, the method includes enabling the operation of the vehicle if the result of the driver's BrAC is below a set point, which may also be done with a processor. In some embodiments, the method includes requesting an active second air sample from the driver and measuring the BrAC of the driver if the result of a passive breath test of a first air sample is at an intermediate level. In some embodiments, the request may be made by a processor. In some embodiments, the method includes continuously measuring air samples after initiating the sensor system, and continuously measuring the concentration of the tracer gas after the first air sample is measured. In some embodiments, the sensors continuously measure air samples after initiating the sensor system, and also continuously measure the concentration of the tracer gas after the first air sample is measured.

In some embodiments, the method and apparatus are designed to accumulate sensor signal information over a series of breaths until a desired confidence level is achieved for the analyte measurement.

In a preferred form of the invention, there is provided a method for passive breath alcohol detection, the method comprising:

A) passively obtaining a first air sample from the air inside the interior of a vehicle;

B) determining the concentration of (i) a tracer gas, and (ii) an analyte present in the first air sample;

C) passively obtaining a second air sample from the air inside the interior of the vehicle;

D) determining the concentration of (i) the tracer gas, and (ii) the analyte present in the second air sample;

E) continuing to passively obtain an N number of air samples from the air inside the interior of the vehicle, and for each air sample obtained, determining the concentration of the tracer gas and the analyte present in the air sample;

F) determining a number of peaks in the concentration of the tracer gas and a number of peaks in the concentration of the analyte present in each of the air samples;

G) determining a confidence interval based on the number of peaks in the concentration of the tracer gas and the number of peaks in the concentration of the analyte; and H) controlling operation of the vehicle based on a function of the confidence interval and the concentration of the analyte present in the air samples.

BRIEF DESCRIPTION OF THE DRAWINGS

Further features of the subject matter of this invention, its nature and various advantages, will be apparent upon consideration of the following detailed description, taken in conjunction with the accompanying drawings, in which like reference characters refer to like parts throughout, and in which.

DETAILED DESCRIPTION OF THE PREFERRED EMBODIMENTS

Background

Figure 1:
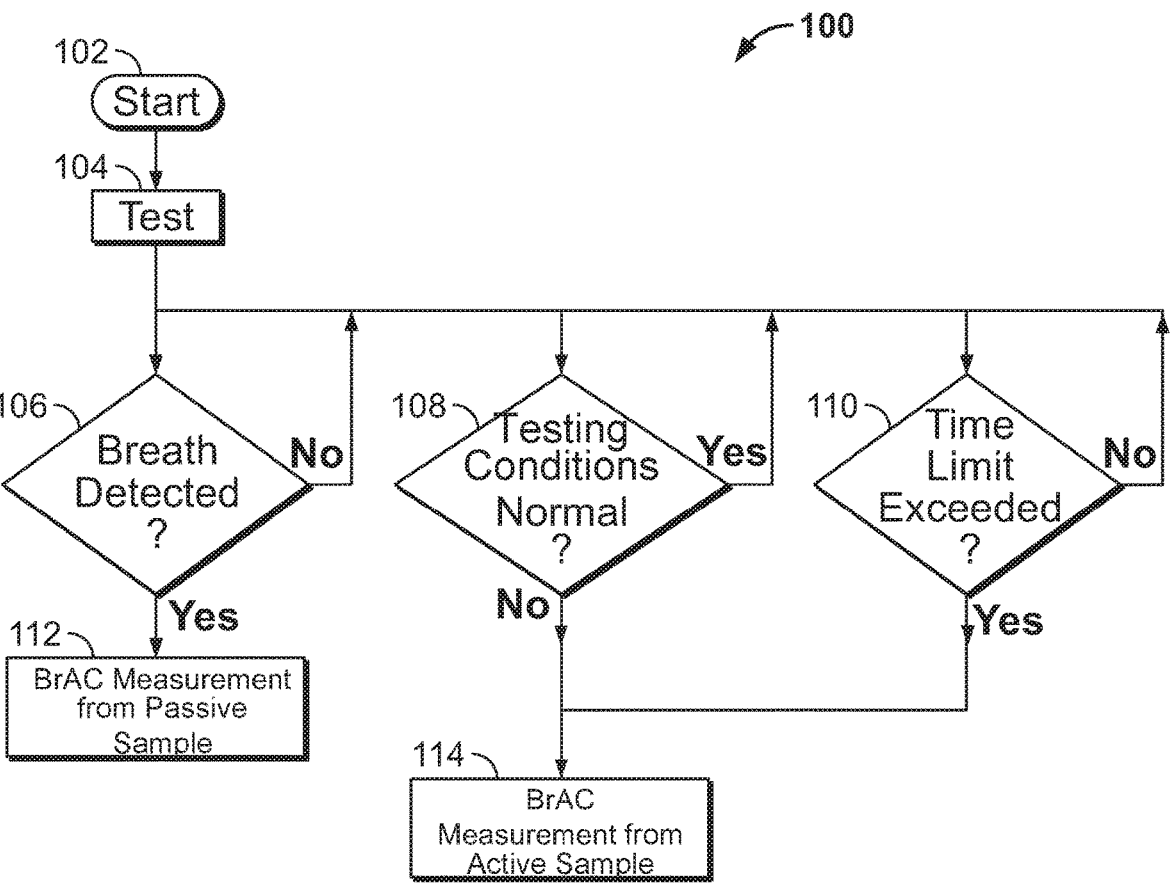
FIG. 1 depicts a flowchart of a process for determining a BrAC measurement from passive or active breath samples, according to an illustrative implementation.

Administering breath tests to drivers is an effective screening method to reduce drunk driving and drunk driving related deaths. In breath testing, a subject exhales air into a sensor or measuring device for a sufficient time and of a sufficient volume to achieve breath flow that originates from the alveoli of the lungs, where substances such as ethyl alcohol (EtOH) in the blood are exchanged with air. The sensor or measuring device then measures the alcohol content in the air (BrAC), which is related to blood alcohol through a conversion algorithm.

Existing breath-based alcohol testing technologies require the driver to deliver a forced expiration approximating full vital capacity. This typically requires substantial time and effort, especially for people with limited lung capacity. For hygienic reasons, the mouthpiece used in existing breath testing devices may also need to be cleaned and replaced after multiple uses. Additionally, environmental conditions, such as wind, temperature, the presence of other people, etc., may significantly affect the accuracy of a BrAC measurement. To improve the adoption and public acceptance of ignition interlock devices in vehicles, a breath testing system that does not inconvenience the driver and is robust under the wide range of conditions found in a vehicle is needed.

There is, therefore, a need for a passive breath test that is flexible enough to avoid inconveniencing the driver while ensuring accuracy of the test under a wide range of environmental conditions and driver behaviors. In a passive breath test, the driver need not provide directed air to the sensor, and the BrAC measurement will be made, without additional action of the driver, from the air within the vehicle, which will be a mixture of breath of both the driver and any passengers, as well as ambient air. In passive breath testing, the air within the vehicle is pulled into the sensor with a fan. The BrAC measurement is made by first measuring the concentration of a tracer gas, such as carbon dioxide, which indicates the dilution of the driver's breath in the air within the vehicle. Then the measured EtOH concentration can be combined with this breath dilution factor to determine a BrAC. The BrAC measurement is thus made without inconvenience to the driver simply through sampling the air within the vehicle.

In contrast, in an active breath test, the driver may be required to be close to the sensor, and to direct a forced, undiluted breath towards the sensor or through an air inlet (e.g., blowing through a tube). In the active breath test, BrAC is thus measured directly from the driver's breath, rather than through the air within the vehicle. The active breath test requires action by the driver separate from the normal actions required to start the vehicle and may thus be considered more inconvenient than the passive breath test.

While a passive breath test is preferred, under some conditions it may not be possible to perform an accurate passive breath test. For example, the driver may attempt to defeat the system, resulting in the air within the vehicle not accurately reflecting the driver's BrAC. Similarly, environmental conditions within the vehicle (such as high wind from open windows, or high temperatures after the vehicle has been standing closed in hot weather) may not allow for accurate BrAC measurement. If normal testing conditions, under which an accurate passive BrAC test is possible, are not met, then an active breath test will be required of the driver.

The present invention provides a variety of sensing checks to allow for passive detection and estimation of a driver's BrAC under normal conditions, while switching to BrAC measurement from an active breath test when normal conditions are no longer met. This reduces driver inconvenience by defaulting to a passive estimation of BrAC, while simultaneously providing alternative logic pathways when the accuracy of a BrAC estimation is non-definitive, or the driver behavior or testing conditions are outside of a norm.

BrAC Measurement from Passive or Active Breath Samples

FIG. 1 depicts a flowchart of a process for determining BrAC measurement from passive or active breath samples, according to an illustrative implementation. The process 100 starts at 102. Start 102 may be initiated by a wireless door key to unlock the vehicle doors, by opening the door to the driver's seat, or any other indicator capable of signaling that a driver has entered a vehicle. As the driver or test subject takes the first steps towards entering the driver seat of the vehicle, process 100 will initiate sensors to monitor the testing conditions within the vehicle, the detection of a driver's breath, and to begin a timer to check whether a driver's breath has been detected within a time limit during testing at 104. If a driver's breath is detected (as determined at logic gate 106), the testing conditions within the vehicle are normal (as determined at logic gate 108), and the time limit has not been exceeded (as determined at logic gate 110), then the process 100 will proceed to 112 and a BrAC measurement from a passive breath sample will be made. However, if either of the logic gates 106 or 108 make a negative determination, or a time limit has been exceeded at 110, then process 100 will proceed to request from the driver an active breath sample at 114.

The testing at 104 includes a self-test of all function blocks and sensors used in the process 100. At testing 104, stable operating temperatures of temperature-sensitive elements of any sensors used in process 100 are established. This may include, for example, the heating of mirrors within a tracer gas detection sensor above 40° C. The mirrors and tracer gas detection sensor are described in further detail with reference to FIG. 4. The self-test procedure conducted at 104 may last between 5-8 seconds in testing conditions at or above room temperature. The self-test procedure may last longer than 8 seconds at low temperatures. The testing at 104 may also entail measuring the initial conditions of the vehicle before the driver has entered, such as $CO_2$ levels, EtOH concentrations in the vehicle air, air temperature, air pressure, etc. These initial conditions may be used to determine, at logic gates 106 and 108, if driver breath has been detected and if the testing conditions are within normal ranges, respectively.

A tracer gas may be any gas used to detect the driver's breath. The tracer gas may be carbon dioxide ($CO_2$) or any other gas that may indicate exhaled breath. The sensitivity of a tracer gas detection sensor allows for detection of highly diluted exhaled breath, which may have a dilution factor (i.e., the ratio between ambient air and undiluted breath) greater than or equal to 50. Air is continuously drawn through the tracer gas detection sensor from the air within the vehicle following initiation of the process 100. The tracer gas detection sensor may be located closer to the position of the driver's head than any passenger position, e.g., at the steering column or side door nearest the driver's side of a vehicle. Exhaled breath is recognized as a signal peak output by the tracer gas detection sensor. If the tracer gas is $CO_2$, the baseline concentration of $CO_2$ corresponding to the baseline signal is expected to be between 400 and 600 ppm (0.04%-0.06% volume). Tracer gas signals and initiation signals for 102 are described in further detail below with reference to FIG. 6. The tracer gas detection sensor, which determines if breath is detected at logic gate 106, is described in further detail below with reference to FIG. 4. The breath sample in which the tracer gas detection peak is found may be the same breath sample used for the BrAC measurement at 112. Thus detecting a driver's breath during testing 104 and the logic gate 106 may occur approximately simultaneously to the BrAC measurement from a passive breath sample made at 112.

Logic gate 108 may process the testing conditions of a vehicle and determine if they are within normal conditions capable of producing an accurate BrAC measurement from a passive breath sample.

Environmental conditions may entail both the behavior of the driver and the state of the vehicle itself. These conditions may be detected by a variety of sensors, including the tracer gas detection sensor, as well as auxiliary sensors placed throughout the vehicle. Sensors may include temperature sensors to determine temperature within the vehicle, and pressure sensors to determine the barometric pressure within the vehicle as well as wind or air moving through the interior of the vehicle. Normal temperatures within a vehicle may be within a range of −40° C. to 85° C. This may be the temperature range over which a BrAC sensor can take accurate passive breath tests. Normal barometric pressure may be within a range of 80 to 105 kPa. This may be the pressure range over which mixing of the driver's breath with ambient air can produce accurate passive breath tests. Temperature and pressure sensors may be any standard sensor element and may be embedded in the body of the vehicle.

A camera sensor to monitor driver behavior may also be placed near the driver, such as close to a steering wheel column. This camera sensor may detect the position of a driver's head with respect to the tracer gas detection sensor, as described in further detail below with respect to FIG. 5. The relation between the driver's head and the tracer gas detection sensor may determine if the driver is breathing in the direction of the tracer gas detection sensor. The camera may detect scenarios in which the driver is attempting to avoid detection of his or her BrAC by facing away from the sensor. The camera sensor may also detect the presence of unfamiliar objects near the driver's face, such as a mask, filter, spray bottle, or other object meant to interfere with the tracer gas detection sensor, or to supply an alternate source of "breath" to prevent an accurate passive breath test. The camera sensor may also detect the close-by position of passengers, which may make it difficult to distinguish between the passenger's BrAC level and the driver's BrAC level, or where the driver is attempting to have the system measure the passenger's BrAC level rather than his or her own BrAC level.

Logic gate 108 may also determine the status of a vehicle's heating, ventilation and air conditioning (HVAC) system, such as whether it is in an ON state or an OFF state. The HVAC system is preferably turned OFF or in a normal operating condition during the process 100. Use of the HVAC system during passive breath testing may excessively dilute the driver's EtOH level, divert the driver's breath away from the sensor, or otherwise prevent an accurate passive breath test. Logic gate 108 may also detect the presence of windshield fluid. Windshield fluid typically includes ethyl alcohol, which may influence the detection of EtOH within the vehicle. The windshield fluid is in an OFF state in normal testing conditions. Logic gate 108 may determine the states of both the vehicle's HVAC system and the state of the windshield fluid through communication with the vehicle, such as with the vehicle's CPU or Controller Area Network (CAN) bus.

The logic gate at 110 determines if a time limit has been exceeded for process 100 to detect the breath of a driver during test 104. This may be a predetermined time limit, such as from 10 to 30 seconds. If more than one tracer peak is detected within the time limit, the average and differences between each BrAC reading may be used for adding confidence to the classification into the classes "high", "intermediate" and "low", as further described below. The accumulated tracer concentration is a major factor in adding confidence by increasing the accumulated signal to noise ratio. More particularly, if more than one peak in the tracer gas concentration is detected within the time limit, the average of a plurality of BrAC concentration measurements (i.e., with each BrAC concentration measurement coinciding with a detected peak in the tracer gas concentration), and the differences between each BrAC reading (i.e., the changes in the areas under each peak for successive BrAC concentration signals), may be used for adding confidence to the classification of the accuracy of the BrAC measurement. By way of example but not limitation, a set of accumulated BrAC concentration measurements taken over a predetermined period of time may be used to calculate the driver's BrAC, with the confidence in the calculated BrAC being classified into the classes "high confidence", "intermediate confidence" and "low confidence", as is hereinafter discussed in further detail. The accumulated tracer gas concentration (i.e., as determined from a plurality of tracer gas concentration measurements) is a major factor in adding confidence by increasing the accumulated signal to noise ratio. If, at 110, it is determined that this time limit has been exceeded, then the process 100 proceeds to a BrAC measurement from an active breath sample at 114. The time limit may prevent situations in which a driver is avoiding breathing in the direction of the sensor, holding his or her breath, has placed a mask over his or her head, or is otherwise attempting to operate a vehicle without providing a breath sample. In this case, the logic gate at 110 will recognize that a breath has not been detected after the predetermined time limit, and will require an active breath sample from the driver at 114.

If, at logic gate 106, the exhaled breath of a driver is detected, while logic gate 108 has determined that testing conditions are normal and logic gate 110 has determined that a time limit has not been exceeded, then process 100 will proceed to measure BrAC from a passive breath sample at 112. BrAC measurement 112 may be described in further detail with reference to FIG. 2. If, however, breath is not detected at 106, then process 100 will continue to test for the breath of the driver until either a time limit is exceeded at 110 or unless normal testing conditions are not met at 108. In this case, process 100 will require an active breath sample at 114 from which BrAC is measured. The determination at 108 that normal testing conditions have not been met is sufficient to require an active breath sample at 114. Similarly, if at 110 it is determined that a time limit has been exceeded, process 100 will proceed to an active breath sample at 114. The active breath sample at 114 may be described in further detail with reference to FIG. 3.

The results of BrAC measurements 112 and 114 may differ in accuracy.

BrAC Measurement from a Passive Breath Sample

Figure 2:
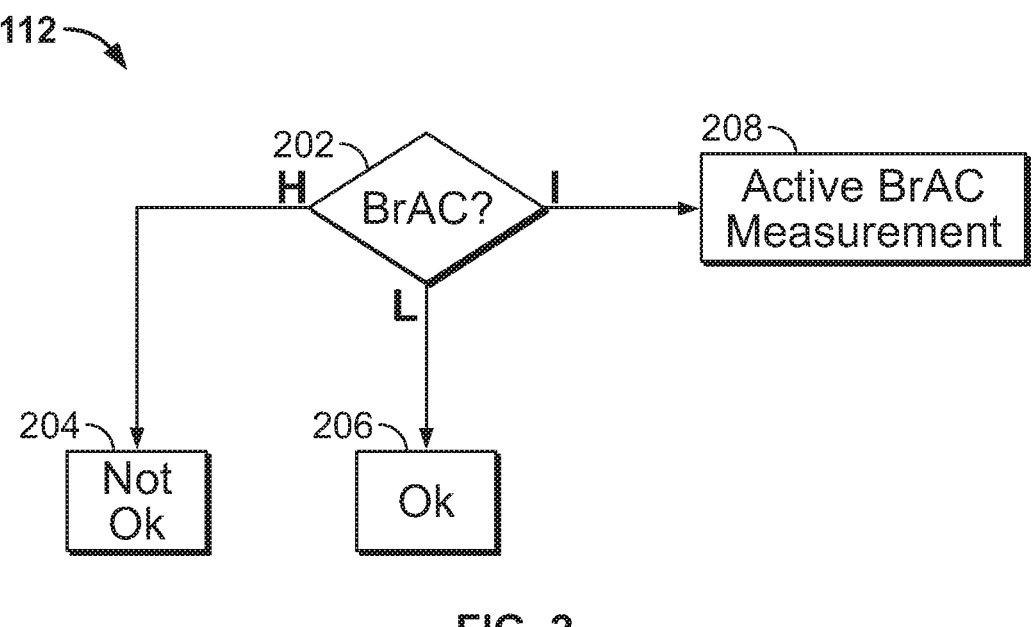
FIG. 2 depicts a flowchart of a process for determining the outcome of a BrAC measurement from a passive breath sample, according to an illustrative implementation.

FIG. 2 depicts a flowchart of a process for determining the outcome of a BrAC measurement from a passive breath sample, according to an illustrative implementation. Process 112 determines a driver's BrAC at 202. Process 112 may be approximately simultaneous to the detection of a tracer gas at 104 and 106, as shown in FIG. 1. Process 112 may thus be carried out using the same breath sample collected at 104 to detect a peak in tracer gas indicating the breath of a driver. Stated another way, if, upon initiation of process 100 a breath is detected at logic gate 106 within the limit of time established at 104, process 112 may proceed to determine the driver's BrAC using the first breath sample recognized at logic gate 106. The measurement of BrAC is based on the dilution of a detected tracer gas, which may be $CO_2$. The detected dilution factor, or DF, of the tracer gas in the vehicle's ambient air is used to determine an estimate of the driver's BrAC. The BrAC level may be determined according to the following equation:

$$BrAC = EtOH * DF \qquad \text{(Equation 1)}$$

DF is the dilution factor of the tracer gas in air, i.e., DF is the ratio between the end expository (undiluted) tracer gas concentration and the tracer gas concentration measured by the sensor. Additional algorithms may be used incorporating information from auxiliary sensors (not shown). The algorithm used measure BrAC from a passive breath sample at 112 is essentially the same as the algorithm used to measure BrAC from an active breath sample at 114. It will be appreciated that DF is much larger when measuring BrAC from a passive breath sample at 112 than when measuring BrAC from an active breath sample at 114. As seen in FIG. 2, if the estimated value of BrAC is below a predetermined set point (denoted "Low" or "L"), then the process 112 outputs a signal at 206 that the BrAC of a driver is "OK." The predetermined set point may be in the interval of 0.1 to 0.4 mg/L (50 to 200 ppm). The predetermined set point may be a function of the driver's age. The predetermined set point may be a function of a legal limit on blood alcohol concentration for driving under the influence (DUI) or driving while impaired (DWI). Signal 206 may be used to enable the operation of a vehicle. If the estimated BrAC value is well above the predetermined set point (denoted "High" or "H"), then the process 112 will output a signal at 204 indicating that the BrAC of a driver is "Not OK." By way of example but not limitation, a BrAC level of 0.1-0.2 mg/L (50 to 100 ppm) above said set point may cause the output of the signal at 204 indicating that the BrAC of the driver is "Not Ok." Signal 204 may be used to disable the operation of a vehicle. If, at 202, it is determined that the BrAC of a driver is within an intermediate range (denoted "Intermediate" or "I") slightly above or below the predetermined set-point, then further analysis of the driver's breath is required to make a final determination. The driver is then asked to perform an active breath test at 208. The active breath test is described in further detail with reference to FIG. 3, and is the process

Figure 3:
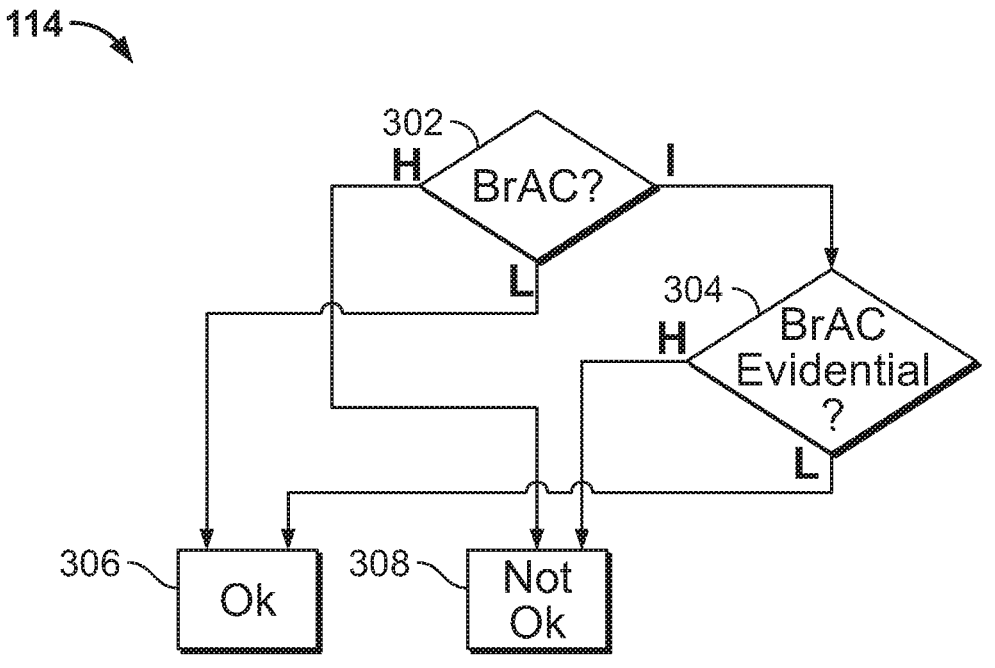
FIG. 3 depicts a flowchart of a process for determining the outcome of a BrAC measurement from an active breath sample, according to an illustrative implementation.

114 as shown in FIG. 1 and FIG. 3. A sensor, such as the sensor described in FIG. 4 may make the measurement at 202, while external processing such as described in further detail in FIG. 4 may communicate the signals 204 and 206 to a central processing unit, or CPU, 415.

BrAC Measurement from an Active Breath Sample

FIG. 3 depicts a flowchart of a process for determining the outcome of an BrAC measurement from an active breath sample, according to an illustrative implementation. Process 114 begins at 302 where the BrAC of a driver is measured. In the BrAC measurement from an active breath sample at 302, a driver is requested to provide an active breath towards a sensor (not shown) at a distance of 15-30 cm from the sensor. The distance may be adjusted for the location of the sensor within the vehicle. If the BrAC is below a predetermined set point (denoted "Low" or "L"), then the process 114 outputs a signal at 306 that the BrAC of a driver is "OK."

Signal 306 may be used to enable the operation of a vehicle. If the estimated BrAC value is well above the predetermined set point (denoted "High" or "H"), then the process 114 will output a signal at 308 indicating that the BrAC of a driver is "Not OK." Signal 308 may be used to disable the operation of a vehicle. If, at 302, it is determined that the BrAC of a driver is within an intermediate range (denoted "Intermediate" or "I") slightly above or below the predetermined set-point, then the driver will be requested to provide a breath sample with evidential accuracy at 304. The breath test performed at 304 will require an undiluted breath sample. From test 304 there is no intermediate response. The breath test at 304 will require the driver to direct an active breath towards a sensor (not shown) at a distance of 15-30 cm from the sensor. The distance may be adjusted for the location of the sensor within the vehicle. If the measured BrAC value is below a set-point (L), then process 114 will produce an output signal at 306 indicating that the BrAC of a driver is "OK." If the measured BrAC value is above a set-point (H), then the process 114 will produce an output signal at 308 indicating that the BrAC of a driver is "Not OK."

The logic gates 106, 108, 110 in FIG. 1, 202 in FIGS. 2, and 302 and 304 in FIG. 3 are shown as representing "IF ... THEN" logical statements, however these logic gates are not restricted to elements of Boolean logic. Logic gates 106, 108, 110, 202, 302 and 304 may also demonstrate fuzzy logic or be governed by artificial neural networks. The desired logic system may be programmed into a CPU 415 as described in further detail with reference to FIG. 4.

Figure 4:
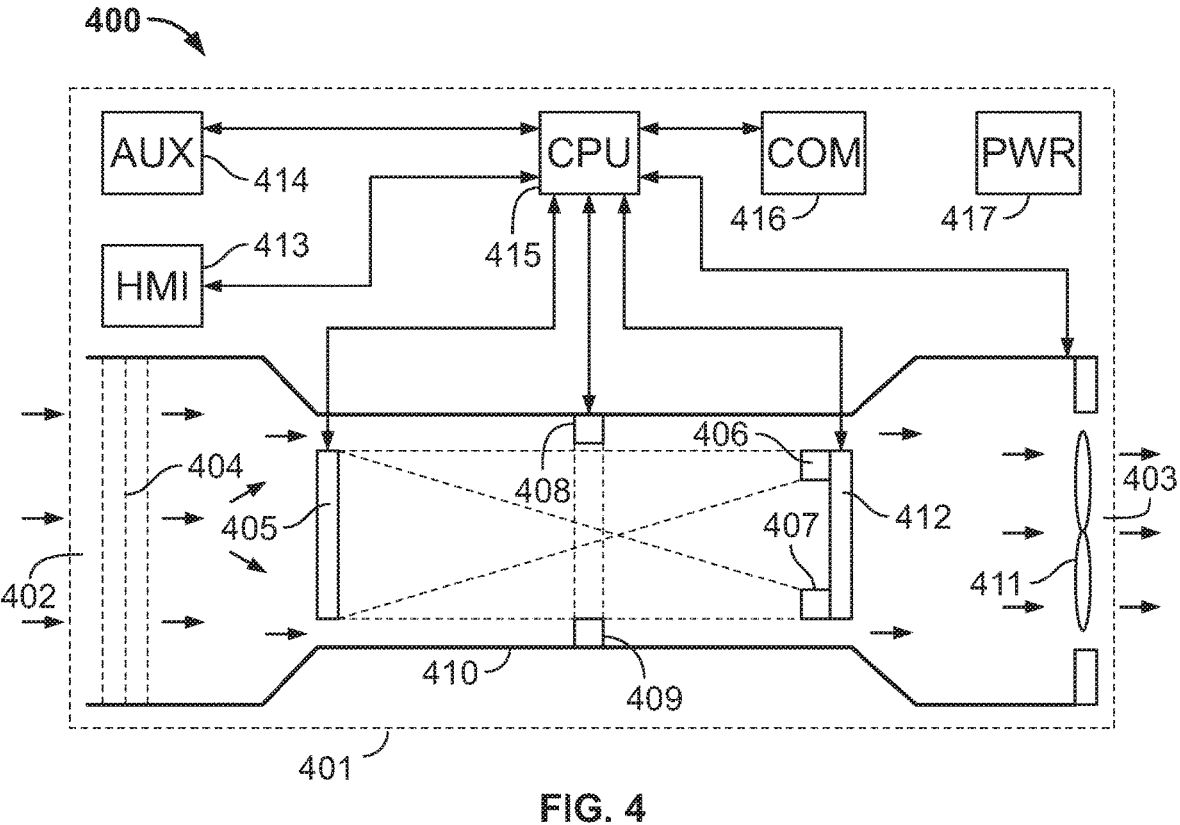
FIG. 4 depicts a sensor for detecting breath and BrAC concentrations from both active and passive breath samples, according to an illustrative implementation.

Sensor for Detecting Breath and BrAC Concentrations from Both Active and Passive Breath Samples FIG. 4 depicts a sensor for detecting breath and BrAC concentrations from both active and passive breath samples, according to an illustrative implementation. The sensor 400 may detect breath during test 104 as shown in FIG. 1, measure initial conditions of the vehicle at 104, as well as perform both the BrAC measurement from a passive breath sample 112 and the BrAC measurement from an active breath sample 114 as shown in FIG. 1, and described in further detail with reference to FIG. 2 and FIG. 3. The sensor 400 draws air continuously through an inlet 402, passing that air to an outlet 403, and measures for both the presence of a tracer gas such as $CO_2$ and the presence of EtOH within the airflow. The sensor 400 determines whether a driver's BrAC is within a Low, High or Intermediate range, as described with reference to FIG. 2 and FIG. 3.

The sensor 400 is contained within an enclosure 401, and may be a stand-alone sensor or designed for integration into the interior of a vehicle, such as within a steering wheel column, a side door, A- or B-vertical support pillars, a sun visor, dashboard, or other convenient position significantly closer to a driver's head than to a passenger-designated area of the vehicle. The enclosure 401 may be airtight except for the openings at the sensor inlet 402 and outlet 403. The enclosure 401 may have the approximate dimensions of 25×40×120 mm. The air brought into the enclosure 401 through the inlet 402 is heated to above body temperature by an inlet heater 404, which may avoid condensation at low ambient temperatures. The inlet heater 404 may have a large surface contact area to the inlet air in order to improve heat transfer from the heater to the incoming air. The heater 404 may be a resistive heater. The air flow from the inlet 402 to the outlet 403 is driven by a fan 411 located close to the outlet 403.

The sensor 400 measures the presence of both $CO_2$ and EtOH through infrared (IR) spectroscopy. IR spectroscopy uses the specific "fingerprint" that gas-phase alcohol produces when illuminated by infrared light to determine an alcohol concentration within the airflow of the sensor 400. The detected absorption spectrum of any substance is a product of resonant molecular vibrations, which are specific to the atomic bonds within a molecule or compound in the breath sample. From the absorption spectrum, particular substances and their absolute or relative concentrations within the breath sample can be determined.

To perform IR spectroscopy and detect both the presence of a tracer gas and the presence of EtOH, the sensor air chamber tube 410 includes two separate optical paths, one for detection of a tracer gas and a second for detection of EtOH. The signals produced by these two optical paths are used to determine the value of a dilution factor of the driver's breath in ambient air (or DF as shown in Equation 1) as well as the value of EtOH concentration within the input air.

The first optical pathway, composed of an EtOH IR emitter 406 and EtOH IR detector 407 as shown in FIG. 4, will determine an EtOH concentration. The EtOH IR emitter 406 outputs IR radiation into the interior of the sensor air chamber tube 410. A spherical mirror assembly composed of a first mirror 405 placed at one end of the air chamber tube 410 and a second mirror 412 located at the opposite end of the air chamber tube 410 reflects the emitted IR radiation from the EtOH IR emitter 406. The optical path length of the emitted IR radiation may be several times that of the distance between the first mirror 405 and the second mirror 412, as the mirror assembly will reflect the emitted light several times before it hits the EtOH IR detector 407. Mirrors 405, 412 preferably include, on their reflecting surfaces, a layer of highly reflecting material, such as gold or aluminum, and a very thin protective surface layer to maintain high reflectance even if the air chamber tube 410 is subjected to corrosive gases during its operating lifetime. The optical path is shown as dashed lines in FIG. 4, however this is shown as an example and the actual optical path between the EtOH IR emitter 406 and the EtOH IR detector 407 may be much longer. Typically, the beam of infrared radiation may traverse the optical cell from the emitter 406 a number of times, e.g., sixteen times (or any multiple of four) before it hits the detector 407.

The EtOH IR emitter 406 may be a black-body radiator, IR laser diode, or any other optical source capable of producing IR light and preferably with a small mass to fit within the air chamber tube 410. The EtOH IR emitter 406 may be modulated at a frequency between 5-10 Hz in order to suppress low frequency noise and disturbances in the signal of the EtOH IR detector 407. The EtOH IR detector 407 includes a bandpass filter that is tuned to the IR absorption peak for EtOH, which is approximately 9.5 μm. The EtOH IR detector 407 may be a pyroelectric or photonic detector, capable of producing a high resolution signal, and may also include a Peltier element for localized cooling in order to suppress thermal noise in the detection signal. The detection signal produced by the EtOH IR detector 407 is described in further detail with reference to FIG. 6. The sensor 400 is specifically designed for high resolution IR spectroscopy measurements, and may have a resolution exceeding 0.5 μg/L (or 1.2 ppm) of EtOH, enabling the estimation of alcohol concentration in highly diluted breath.

The second optical pathway is dedicated to detecting the presence of a tracer gas, such as $CO_2$, which will indicate the dilution of a driver's breath within the air input through the sensor 400. A tracer gas IR emitter 408 is placed opposite a tracer gas IR detector 409 such that the optical path from the tracer gas IR emitter 408 to the tracer gas IR detector 409 is across the shorter dimension of the air chamber tube 410. The tracer gas IR detector 409 may be tuned to a wavelength band specific to the IR absorption frequency of the detected tracer gas. In an example where the tracer gas is $CO_2$, the absorption peak may be at 4.26 μm. Due to the high end tidal concentration of $CO_2$ in exhaled air, which is typically at 4.2% volume, a short optical path across the air chamber tube 410 may be used. This path is indicated in FIG. 4 as a dashed line between the tracer gas IR emitter 408 and the tracer gas IR detector 409. The signal produced by the tracer gas IR detector is described in further detail with reference to FIG. 6.

The signals from both EtOH IR detector 407 and tracer gas IR detector 409 may be used to determine if normal conditions for the passive measurement of BrAC are met, such as during the test 104 and the logic gate 108 of process 100 as shown in FIG. 1. This process may entail checking that the baseline presence of the tracer gas is within standard levels, such as the baseline concentration of $CO_2$ in ambient air.

The first mirror 405 and the second mirror 412 are both in communication with a central processing unit, or CPU, 415 as shown in FIG. 4. The EtOH IR emitter 406, EtOH IR detector 407, tracer gas IR emitter 408 and tracer gas IR detector 409 may also be in signal communication with the CPU 415. CPU 415 processes the signal generated by the EtOH IR detector 407 and the tracer gas IR detector 409 to determine BrAC measurements.

A Human-Machine Interface (HMI) 413 is in communication with the CPU 415 and may be used to communicate with a driver to request an BrAC measurement from an active breath sample. The HMI 413 includes audiovisual means for communication with a driver, such as a screen and speakers, to convey messages and a request for an active breath test, as well as other directions, to a driver. The HMI 413 may display the result of a BrAC measurement to the driver. The HMI 413 may be a multi-purpose interface, such that requesting and displaying information related to a breath test is only one of many functions. Other functions may be navigation, HVAC interaction, stereo system interaction, or other system interactions typical for a vehicle. The HMI 413 may be integrated into the vehicle within view of the driver.

The CPU 415 is also in communication with auxiliary sensors 414, which may be, for example, temperature, barometric pressure or optical sensors, or a camera to determine the testing conditions within a vehicle. The auxiliary sensors 414 are used during the test 104 of process 100. A data communication unit 416 may store parameter values used by the CPU to determine BrAC measurements and normal testing conditions of the vehicle. The data communication unit 416 also transfers data between the sensor system 400 and other units outside of the sensor 400 (not shown). The sensor 400 also includes a power unit 117 for power management and supply.

Measuring Head Position

Figure 5A:
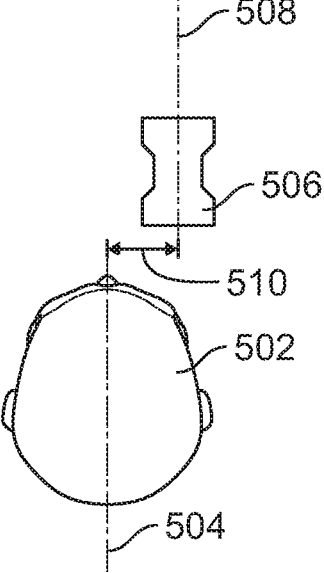
FIGS. 5A and 5B are an overhead view of a driver's head position in relation to a sensor, according to an illustrative implementation.

FIG. 5A is an overhead view of a driver's head position in relation to a sensor, according to an illustrative implementation. Auxiliary sensors measure a lateral distance 510 between the driver 502 and the sensor 506. The lateral distance 510 may be measured between the midline 508 of the sensor 506 and the midline 504 of the driver's head 502. Under normal testing conditions, the lateral distance 510 is less than or equal to 20 cm. The measurement of lateral distance 510 may occur at the test 104 of process 100 as shown in FIG. 1. The determination at logic gate 108 if testing conditions of the vehicle are normal takes into account the lateral distance 510 as shown in FIG. 5A. Measurement of the lateral distance 510 may ensure that the driver is breathing directly towards the sensor 506 during an active breath test. Measurement of lateral distance 510 may also ensure that during passive breath testing, the driver is not attempting to avoid breath detection of the sensor by holding his or her head away from the direction of the sensor.

Figure 5B:
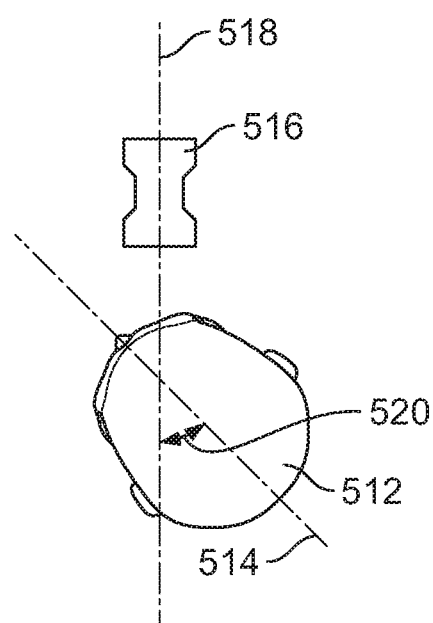

Looking next at FIG. 5B, auxiliary sensors also measure a driver's head rotation in relation to the midline 518 of sensor 516. The rotational angle 520 may be measured between the midline 518 of the sensor 516 and the midline 514 of the driver's head 512. Under normal testing conditions, the rotational angle 520 may be ±5°. The measurement of the rotational angle 520 may occur at the test 104 of process 100 as shown in FIG. 1.

The determination at logic gate 108 of whether or not testing conditions of the vehicle are normal takes into account the rotational angle 520 as shown in FIG. 5B. Measurement of the rotational angle 520 may ensure that the driver is breathing directly towards the sensor 516 during an active breath test. Measurement of the rotational angle 520 may also ensure that during passive breath testing, the driver is not attempting to avoid breath detection of the sensor by holding his or her head away from the direction of the sensor.

The lateral distance 510 and rotational angle 520 may be measured by an embedded camera sensor (not shown), which may be incorporated into a vehicle and placed near a driver's head. The embedded camera may also determine if there is an unfamiliar object within the camera's field of view, and/or whether a passenger is within field of view of a driver's head.

Signals Detected by an Initiation Sensor and a BrAC Sensor

Figure 6:
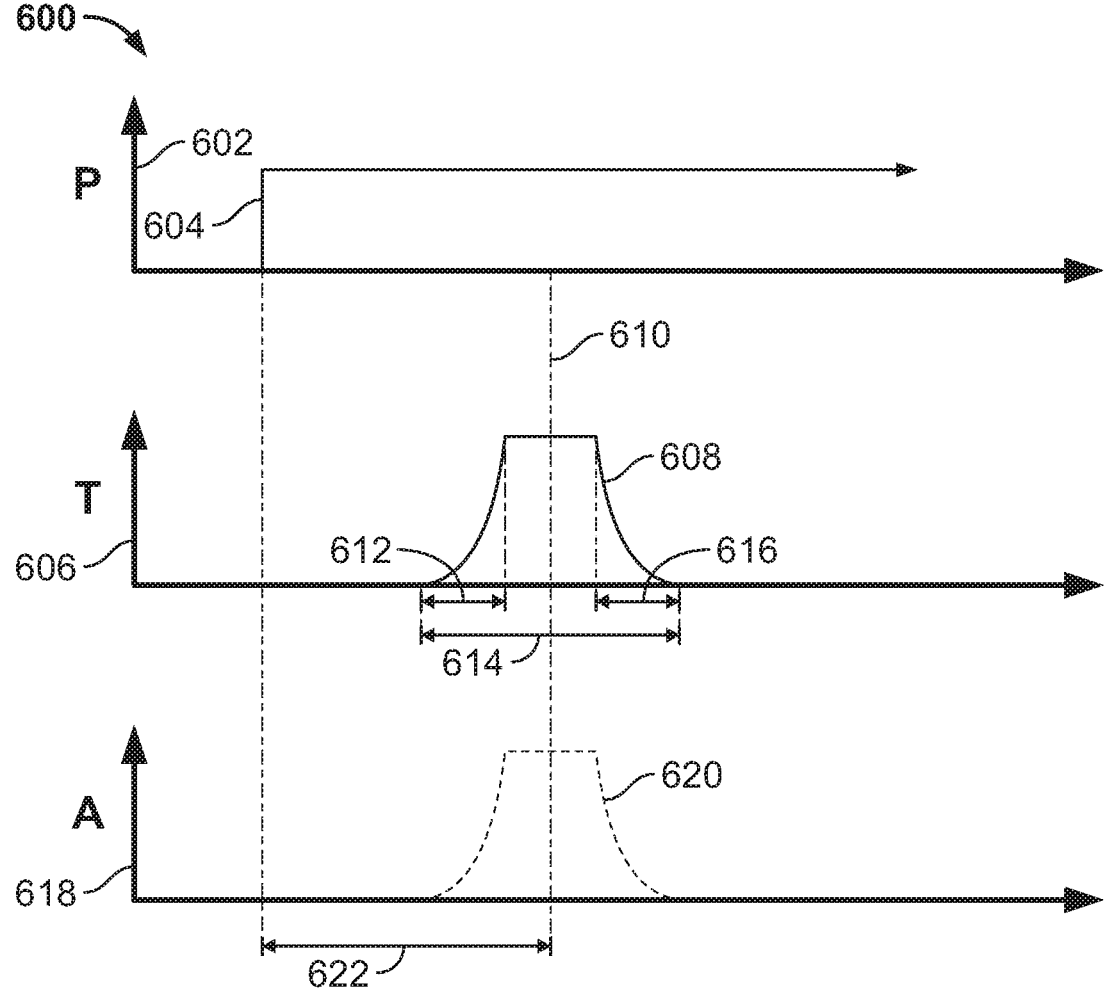
FIG. 6 is a graph representing examples of signals detected by an initiation sensor and a BrAC sensor, according to an illustrative implementation.

FIG. 6 is a graph representing examples of signals detected by sensor 400 using the illustrative implementation of the present invention shown in FIG. 4. The graphs shown at 600 occur along the same time scale. Graph 602 (denoted "P") shows a signal 604 representing the detection of the presence of a driver as he or she enters or prepares to enter a vehicle (e.g., as detected by auxiliary sensor 414). Signal 604 initiates the start 102 as shown in process 100 in FIG. 1. Signal 604 begins a timer that will determine the time interval between the initiation signal at 604 and the detection of a breath, which is shown at graph 606 (denoted "T"). Breath is detected from a peak 608 in the concentration of a tracer gas signal. When the tracer gas is $CO_2$, a peak in breath detection is characterized by a magnitude of $CO_2$ detection at or above 525 ppm, assuming a dilution factor of 80, and assuming an end-tidal $CO_2$ concentration of 4.2% volume. The duration 614 of the peak 608 is expected to be 1-3 seconds, excluding the response time of the sensor. The rise time of the peak 612 as well as the decline time 616 may also be used to characterize the tracer gas signal as the result of exhaled breath of a driver. Typical rise times may be in the range 0.5 to 1.0 seconds, while typical decline times may be in the range 3 to 5 seconds. The peak in the tracer gas signal at 610 may end the timer. The time interval 622 may be measured and used to determine if an acceptable time limit has been exceeded between the initiation signal 604 and point 610 in the breath signal 608, such as at logic gate 110 as shown in FIG. 1.

Graph 618 (denoted "A") shows the detection signal for EtOH. Depending on the concentration of EtOH within a driver's breath, graph 618 may or may not show a peak 620 corresponding to the peak 608 in the tracer gas. If, however, there is EtOH in the driver's breath, the EtOH signal 620 will be approximately simultaneous to the tracer gas signal 608, as shown in FIG. 6. The magnitude of the peak in the EtOH signal 620 will indicate the concentration of BrAC in the measured breath sample. Measurement of BrAC from peak 620 may occur approximately simultaneously to the detection of peak 608 in the tracer gas signal.

Passive BrAC Estimation Using Accumulating Sensor Signal Acquisition

In the forgoing sections, the estimation of BrAC is performed by the combined use of sensor signals representing a tracer gas, for example, carbon dioxide ($CO_2$), and ethyl alcohol vapor (EtOH). The invention is, however, not limited to these substances, or to the specific location of a test subject (e.g., a driver in a driver's seat). It could be used in any situation where it is critical to accurately estimate the breath concentration of any specific substance without interfering with the subject being tested.

As described above, passive estimation of breath alcohol concentration (BrAC) can be performed by measuring the tracer gas concentration at the same location and performing the following calculation $$BrAC = EtOH * DF \qquad \text{(Equation 1)}$$

where DF denotes the dilution factor determined by the end expiratory concentration of the tracer gas divided by the measured value at the sensor location. In the case of $CO_2$ as the tracer gas, the end expiratory concentration is 4.2 vol %, and the corresponding value for water vapor is 5.5 vol %. In passive in-vehicle applications, DF may vary considerably.

The foregoing sections disclose a method and apparatus for passive detection of an analyte (e.g., EtOH) by the management of conditions related to signal stability, environmental influences and subject behavior, all of which are necessary for an accurate analyte estimation. When these conditions deviate from normal, the accuracy of the passive detection process may be diminished and the subject is required to provide an active breath sample.

In the following section, there is disclosed a modified method and apparatus for passive detection of an analyte (e.g., EtOH). This modified method and apparatus can produce a more accurate estimation of an analyte (e.g., EtOH). This modified method and apparatus is essentially based on the premise that the confidence level of the analyte assessment increases as the amount of analyzed gas increases, i.e., accumulating sensor signal information over a series of breaths can increase the confidence level of the analyte measurement.

Some of the key features of this modified method and apparatus include:

- means to determine, and to repetitively record, the instantaneous tracer gas concentration at a location in the proximity of the driver's seat of a vehicle;
- means to determine, and to repetitively record, the instantaneous alcohol vapor concentration in synchronism with, and at the same location as the recording of the tracer gas concentration;
- means to quantify the magnitude and timing of peaks of the tracer gas concentration;
- means to calculate the cumulative breath alcohol concentration based on the peak magnitudes and timing of the peaks of the tracer gas (i.e., by using instantaneous tracer gas and alcohol vapor concentrations);
- means to calculate the cumulative confidence level over time of the breath alcohol concentration; and
- means to activate an alarm and/or switch enabling and/or disabling the driving of the vehicle according to the combined result of the calculation of average breath alcohol determination and the confidence level in relation to a preset limit concentration.

In essence, this form of the invention recognizes that the confidence level of the analyte determination increases as the quantity of the analyzed gas increases, i.e., the confidence level of the analyte determination increases as the number of analyzed breaths increases.

Figure 7:
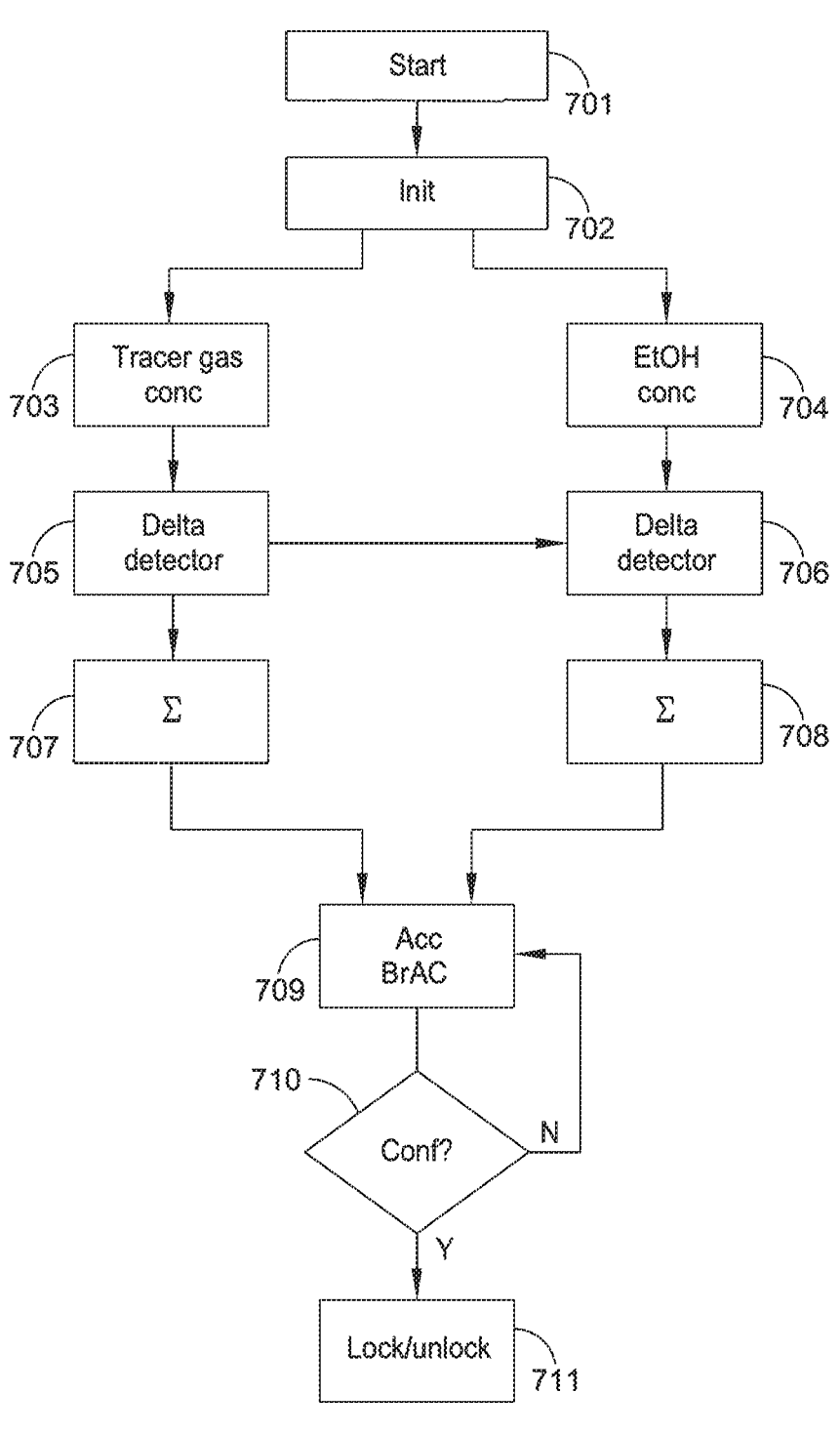
FIG. 7 is a flowchart showing one method for accumulating sensor signal information over a series of breaths until a desired confidence level is achieved for the analyte measurement.

Looking now at FIG. 7, there is shown a signal flowgraph corresponding to one embodiment of a modified method and apparatus for estimating BrAC. The system is started at 701 by unlocking the vehicle cabin door, and the initiation phase 702 includes self-test procedures to check the operation of all system components. These procedures are normally fast and the system is quickly capable of continuously recording sensor signals corresponding to (i) local tracer gas concentration 703 and (ii) EtOH concentration 704. When the driver enters the vehicle cabin and delivers an expired breath, a tracer gas peak will appear at the sensor location, and the magnitude and timing of this peak will be determined by the delta detector 705. The timing is used for triggering the determination of the magnitude of a corresponding EtOH peak by the delta detector 706. A more detailed description of the function of the delta detectors 705, 706 is provided below in relation to FIG. 9.

The tracer gas and EtOH signals 703, 704 are continuously recorded. As time is elapsing, more signal peaks corresponding to expired breaths from the driver will be recorded and accumulated by adding contributions from each detected peak by means of adder block 707 for the tracer gas signal and the adder block 708 for the EtOH signal.

The adder block signals 707, 708 are combined to enable the accumulated BrAC calculation 709 using the equation:

$$\sum\nolimits_{i=1}^{n} \frac{\dfrac{1}{DF_i}}{\sum\nolimits_{j=1}^{m} \dfrac{1}{DF_j}} BrAC_i \qquad \text{(Equation 2)}$$

Which equation may also be restated as:

$$\sum\nolimits_{i=1}^{n} \frac{EtOH_i}{\sum\nolimits_{j=1}^{m} \dfrac{1}{DF_j}} \qquad \text{(Equation 3)}$$

With both Equation 2 and Equation 3, the $CO_2$-dependent dilution factor (DF) is the quality indicator. Thus it will be appreciated that with both Equation 2 and Equation 3, the smaller the value of the $CO_2$-dependent dilution factor (DF), i.e., corresponding to a higher measured $CO_2$ value, the greater the corresponding peak is weighted in Equations 2 and 3.

The confidence of the BrAC value is then tested in block 710 with respect to (i) criteria based on the legal limit value or any other preset limit value (e.g., a BrAC value of 0.08% or less may be required to operate a vehicle in the U.S., a different BrAC value may be required to operate a vehicle outside the U.S., etc.), and (ii) the required confidence level in the calculated accumulated BrAC, which may vary from one application to another, e.g., a "high confidence level" may be required when the BrAC value is very close to (e.g., slightly above or slightly below) the legal limit for a given jurisdiction, an "intermediate confidence level" may be required when the BrAC value is greater than zero, but still significantly below the legal limit for a given jurisdiction, a "low confidence level" may be required when the BrAC value is significantly below (or significantly above) the legal limit for a given jurisdiction, etc. If the required confidence level (e.g., "high confidence level", "intermediate confidence level" or "low confidence level") for a particular application is achieved, then the final lock/unlock function 711 is reached determining the drivability of the vehicle. If the required confidence level is not achieved, additional accumulation of BrAC determinations 709 will be required (i.e., the system will continue to acquire BrAC information from additional exhalations of the driver until a desired confidence level is achieved). Note that various factors may influence the confidence levels associated with the determination of analyte concentration, and these factors include, but are not limited to, sensor sensitivity, the number of breaths sampled, signal stability, environmental influence and subject behavior, etc. Note also that the confidence level ascribed to an accumulated BrAC value is a function of the number of breaths analyzed to arrive at the accumulated BrAC value which is, in turn, represented by the number of peaks in the tracer gas concentration that are measured.

Figure 8:
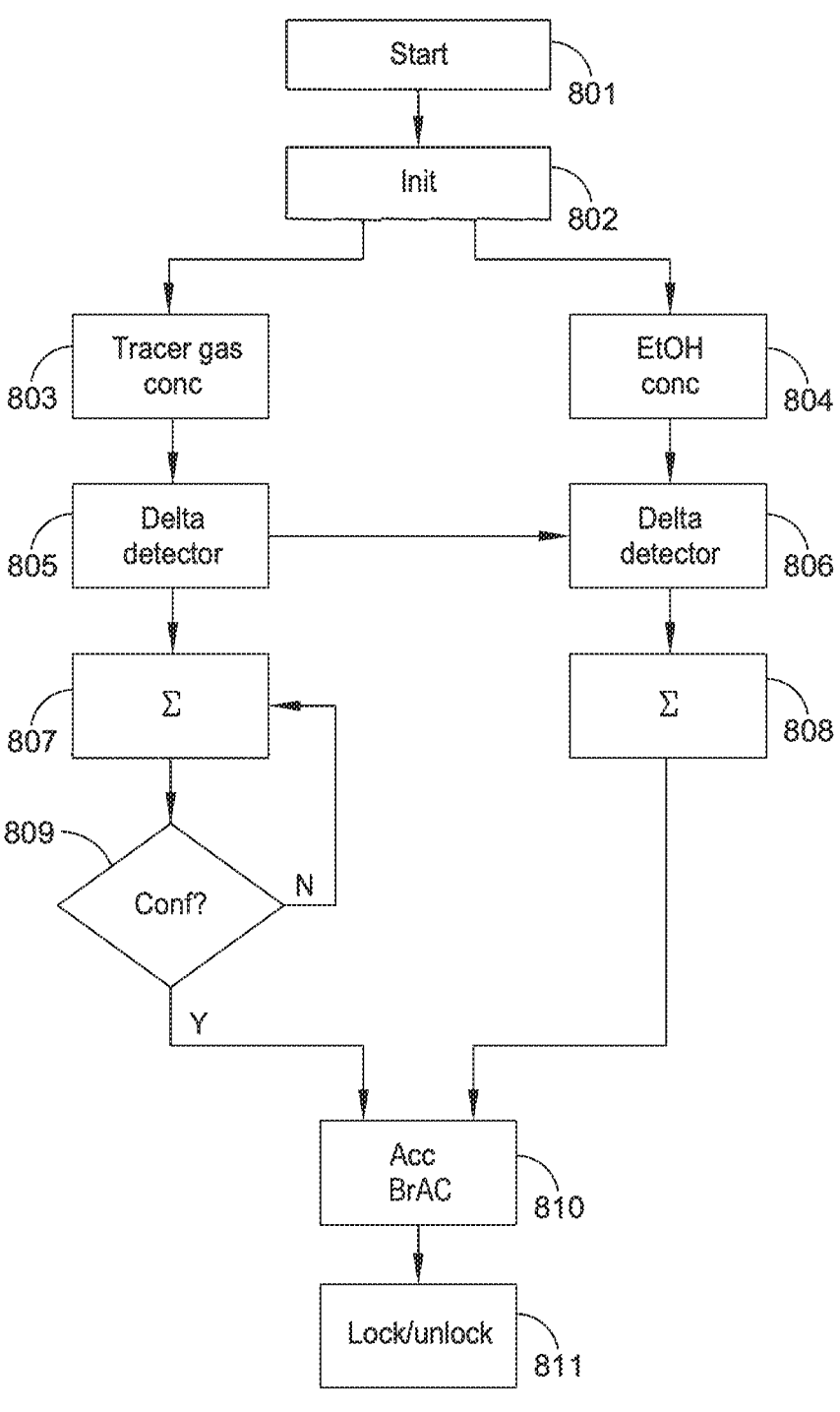
FIG. 8 is a flowchart showing another method for accumulating sensor signal information over a series of breaths until a desired confidence level is achieved for the analyte measurement.

In another form of the invention, and looking now at FIG. 8, the implementation of the confidence block 809 is somewhat different and is based on the tracer gas signal only. In this implementation of the invention, and as will be discussed in more detail below, BrAC determination 810 is only performed when the accumulation of tracer peaks has reached a certain preset limit value based on test results performed on the system. The lock/unlock function 811 is identical to the lock/unlock function 711.

Thus, in this form of the invention, and still looking at FIG. 8, the system is started at 801 by unlocking the vehicle cabin door, and the initiation phase 802 includes self-test procedures to check the operation of all system components. These procedures are normally fast and the system is quickly capable of continuously recording sensor signals corresponding to local tracer gas concentration 803 and EtOH concentration 804. When the driver enters the vehicle cabin and delivers an expired breath, a tracer gas peak will appear at the sensor location, and the magnitude and timing of this peak will be determined by the delta detector 805. The timing is used for triggering the determination of the magnitude of a corresponding EtOH peak by the delta detector 806. Again, a more detailed description of the function of the delta detectors 805, 806 is provided below in relation to FIG. 9.

The tracer gas and EtOH signals 803, 804 are continuously recorded. As time is elapsing, more signal peaks corresponding to expired breaths from the driver will be recorded and accumulated by adding contributions from each detected peak by means of adder block 807 for the tracer gas signal and the adder block 808 for the EtOH signal.

The confidence of the tracer gas value is then tested in block 809 with respect to (i) criteria based on the legal limit value or any other preset limit value (e.g., a BrAC value of 0.08% or less may be required to operate a vehicle in the U.S., or a different BrAC value established by law for a different jurisdiction, or another BrAC value set by a the vehicle manufacturer, etc.), and (ii) the required confidence level (e.g., a "high confidence level", "intermediate confidence level" or "low confidence level"). If the required confidence level is achieved, then the adder block signals 807 and 808 are combined to enable the accumulated BrAC calculation 810 using the equation BrAC=EtOH*DF. Note that Equations 2 and 3 may be used when it is desired to ascribe to the accumulated BrAC value a higher statistical weight for readings where there is a higher peak in the tracer gas ($CO_2$) concentration than for readings where there is a lower peak in the tracer gas ($CO_2$) concentration. It will be appreciated that when calculating the accumulated BrAC value, higher statistical weight should be attributed to readings with a high tracer gas concentration compared to those with a low tracer gas concentration (i.e., because EtOH concentration signals corresponding with a higher tracer gas concentration signal are likely to be more indicative of a breath in the chamber than EtOH concentration signals corresponding with a lower tracer gas concentration signal, which may be indicative of a partial/over-diluted breath being present in the chamber). If the required confidence level is achieved, then the final lock/unlock function 811 is reached determining the drivability of the vehicle. If the required confidence level is not achieved, additional accumulation of BrAC determinations 810 will be required (i.e., the system continues to acquire tracer gas information from additional exhalations of the driver until a desired confidence level is achieved). Note that various factors may influence the confidence levels associated with the determination of analyte concentration, and these factors include, but are not limited to, sensor sensitivity, the number of breaths sampled, signal stability, environmental influence and subject behavior, etc.

Figure 9:
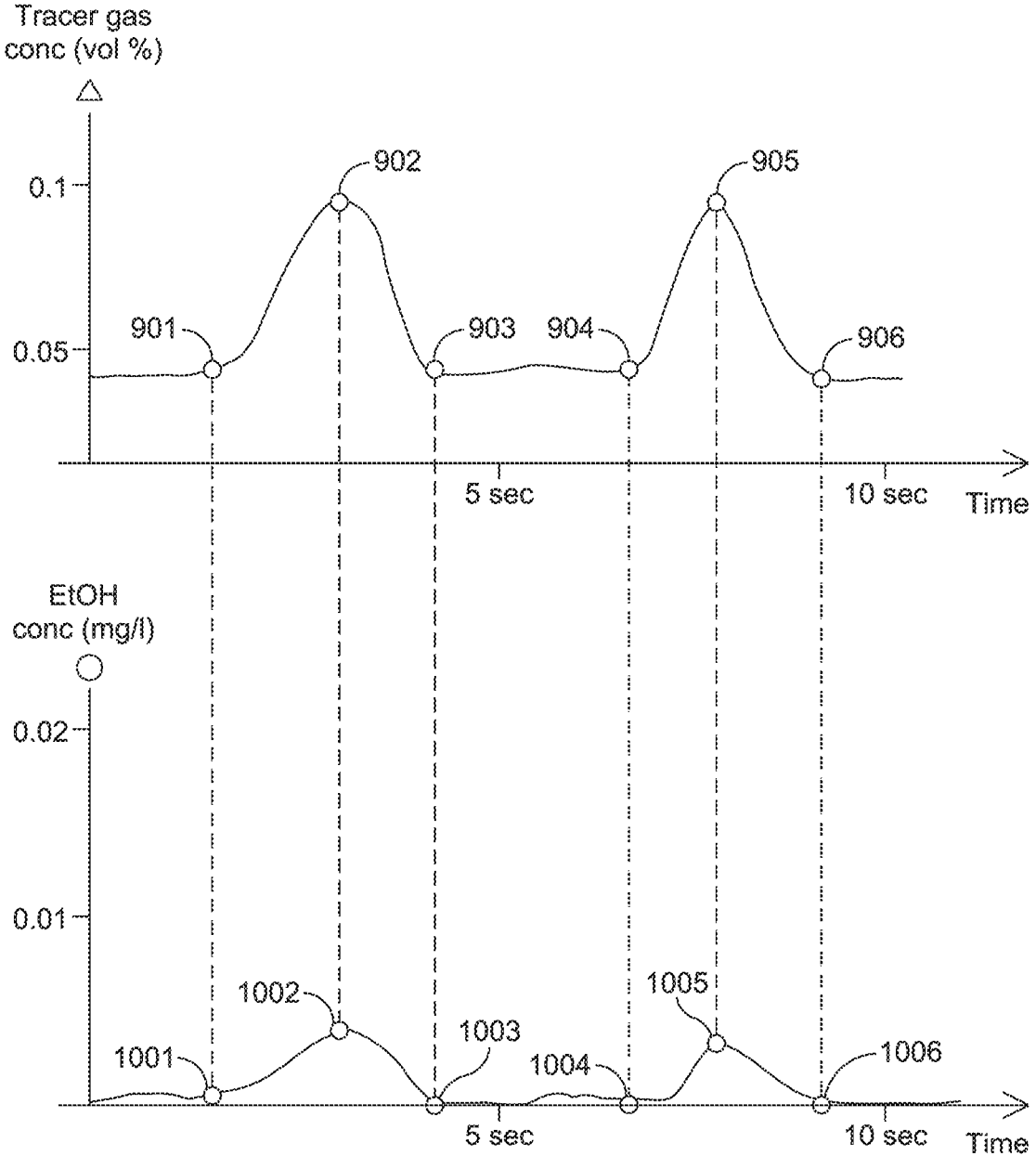
FIG. 9 is a graph representing examples of signals detected by an initiation sensor and a BrAC sensor, according to another illustrative implementation.

FIG. 9 schematically shows typical tracer gas and EtOH concentration signals as a function of time. These tracer gas and EtOH concentration signals correspond to the outputs from the blocks 703, 803, and 704, 804, respectively, in FIGS. 7 and 8, respectively. As seen in FIG. 9, two peaks are observed in both the tracer gas and the EtOH signals after approximately 3 and 8 seconds from the starting point. The peaks correspond to expired breaths from the subject. Note that the two peaks 902, 905 in the tracer gas signal are detected by the delta detector 705, which is essentially a slope detector for finding the peaks in the tracer gas signal. The tracer gas and EtOH signal samples, preferably recorded at a rate of more than five samples per second, are subjected to additive and subtractive operations in real time to detect movements upwards or downwards, thereby enabling the detection, time of occurrence and quantification of peaks above a more or less noisy background. The tracer signal features are peaks 902 and 905, surrounded by background values 901, 903, and 904, 906, respectively, obtained immediately before and after each peak. From these values, it is possible to calculate the magnitudes of the peaks. The use of multiple background points allows for the continuous monitoring of background variations, which may be important for the selection of schemes according to FIGS. 7 and 8 (see below). The variations of the background signal may be referred to as "noise". Such "noise" may be both fundamental in origin, and/or dependent upon environmental factors, such as temperature, humidity, transients, etc. Preferably, "noise" is measured in real time by continuous and automatic sampling of both the tracer gas and EtOH signals in between periods of peak detection and quantification. By comparing, for example, the Root Mean Square (RMVS) variation of the signals, the noise level may be quantified and related to the calculated BrAC peak levels.

A BrAC reading will result from the tracer gas and EtOH signal peak values using Equation (1). If this reading is much higher (or lower) than the legal concentration limit, the BrAC reading may be used directly to classify between "high concentration" or "low concentration", supported by a comparison to the actual noise level. In the "intermediate concentration" cases, the actual noise level will also provide adequate decision support. The BrAC reading, read in conjunction with the legal limit for the particular jurisdiction in question and the noise level, will thus determine the level of confidence in classifying the breath alcohol concentration as being "high confidence level", "intermediate confidence level" or "low confidence level". By adding more BrAC readings, the confidence level of the BrAC measurement increases (e.g., from a "low confidence level" to an "intermediate confidence level" or a "high confidence level").

Combined with data concerning systematic measurement errors, the noise level may be used for defining the confidence level of a BrAC reading using Equation (1).

The timing of the events 901-906 in the tracer gas signal may connect them with corresponding points in time in the EtOH signal, 1001-006, and enable calculation of the corresponding EtOH peak magnitudes (i.e., the EtOH peaks 1002, 1005 correspond in time to the tracer gas peaks 902, 905, respectively, and the EtOH background values 1001, 1003, 1004 and 1006 correspond in time to the tracer gas background values 901, 903, 904 and 906, respectively; note also that the two peaks 1002, 1005 in the EtOH signal are detected by one delta detector 806, which is essentially a slope detector for finding the peaks in the EtOH signal). From the magnitude of the tracer gas peaks in FIG. 9 (i.e., peaks of approximately 0.1), DF may be estimated to be approximately 80, allowing for an estimation of BrAC=0.25 mg/L, according to the aforementioned Equation 1.

If the BrAC values based on the first and second peak would differ such that classification between "high", "intermediate" and "low" concentration with respect to the legal limit cannot be made within a specified confidence level (e.g., a "high confidence level", an "intermediate confidence level", or a "low confidence level"), an active breath test may be required to be obtained from the driver, or an overruling principle, e.g., one of minimizing risk of human injury, may be used to determine the drivability of the vehicle (e.g., halting drivability of the vehicle until the BrAC is determined to be below the legal limit for that particular jurisdiction with a "high" level of confidence).

The procedure described above will automatically compensate for slow variations of the background value in both tracer gas and EtOH channels. The use of continuous or digitized signal acquisition followed by signal accumulation provides enhancement of the signal-to-noise ratio.

The system outline in FIG. 8 may be advantageous when there is a stable background tracer gas concentration (which may be identifiable by relatively stable background values 901, 903 and 904, 906). In such as case there will be very strong correlation between the two signals (i.e., between the tracer gas signal and the EtOH signal). In the presence of passengers, or other external sources of background variations, the scheme shown in FIG. 7 may be more advantageous.

In essence, the present invention comprises a novel method and apparatus for utilizing a plurality of passive breath tests to determine whether a driver's calculated BrAC concentration (i.e., the accumulated BrAC concentration) is generally classified as a "high" concentration BrAC or a "low" concentration BrAC. Additionally, the present invention allows for the determination of whether the accumulated BrAC concentration is ascribed an appropriate confidence level (e.g., "high confidence level", "intermediate confidence level", "low confidence level") for a particular classification of the BrAC concentration, which confidence level is, in part, a function of the total number of breaths analyzed to arrive at the accumulated BrAC concentration.

Modifications of the Preferred Embodiments

It will be understood that the foregoing is only illustrative of the principles of the invention, and that the invention can be practiced by other than the described embodiments, which are presented for purposes of illustration and not of limitation, and the present invention is limited only by the claims which follow.

What is claimed is:

1. A method for passive breath alcohol detection, the method comprising:
- A) passively obtaining a first air sample from the air inside the interior of a vehicle;
- B) determining the concentration of (i) a tracer gas, and (ii) an analyte present in the first air sample;
- C) passively obtaining a second air sample from the air inside the interior of the vehicle;
- D) determining the concentration of (i) the tracer gas, and (ii) the analyte present in the second air sample;
- E) continuing to passively obtain an N number of air samples from the air inside the interior of the vehicle, and for each air sample obtained, determining the concentration of the tracer gas and the analyte present in the air sample;
- F) determining a number of peaks in the concentration of the tracer gas and a number of peaks in the concentration of the analyte present in each of the air samples;
- G) determining a confidence interval based on the number of peaks in the concentration of the tracer gas and the number of peaks in the concentration of the analyte; and

- H) controlling operation of the vehicle based on a function of the confidence interval and the concentration of the analyte present in the air samples, by providing a signal to the vehicle.

2. The method according to claim 1 wherein passively obtaining an air sample from the interior of the vehicle is initiated by using a wireless door key to unlock a door of the vehicle.

3. The method according to claim 1 wherein passively obtaining an air sample from the interior of the vehicle is initiated by a person sitting in a driver's seat of the vehicle.

4. The method according to claim 1 wherein, before proceeding to Step (A), the method comprises initiating sensors to monitor the testing conditions within the vehicle when a driver enters the vehicle and obtaining a test sample from the interior of the vehicle.

5. The method according to claim 4 wherein the initiation of the sensors to monitor the testing conditions within the vehicle comprises at least one from the group consisting of:
- (i) determining whether the tracer gas has been detected in the test sample;
- (ii) determining whether testing conditions are within predetermined parameters; and
- (iii) determining whether a predetermined time after initiation of the sensors to monitor the testing conditions has elapsed.

6. The method according to claim 5 wherein, when all of the following conditions are satisfied:
- (i) a tracer is detected in the test sample;
- (ii) the testing conditions are all within predetermined parameters; and
- (iii) the predetermined time after initiation of the sensors to monitor the testing conditions has not elapsed;
- proceeding to Step (A).

7. The method according to claim 5 where, when any of the following conditions are not satisfied:
- (i) a tracer is detected in the test sample;
- (ii) the testing conditions are all within predetermined parameters; and
- (iii) the predetermined time after initiation of the sensors to monitor the testing conditions has not elapsed;
- performing an active breath test.

8. The method according to claim 5 wherein the testing conditions comprise at least one selected from the group consisting of $CO_2$ level in the air within the interior of the vehicle, EtOH concentration in the air within the interior of the vehicle, the temperature of the air within the interior of the vehicle, the air pressure of the air within the interior of the vehicle, and the location of the driver's head relative to a tracer gas detection sensor.

9. The method according to claim 8 wherein, when the temperature of the air within the interior of the vehicle is between −40° C. and 85° C., the testing condition is satisfied, and when the temperature of the air within the interior of the vehicle is less than −40° C. or greater than 85° C., the testing condition is not satisfied.

10. The method according to claim 8 wherein, when the air pressure of the air within the interior of the vehicle is between 80 kPa and 105 kPa, the testing condition is satisfied, and when the air pressure of the air within the interior of the vehicle is less than 80 kPa or greater than 105 kPa, the testing condition is not satisfied.

11. The method according to claim 8 wherein a camera is used to determine the position of the driver's head relative to the tracer gas detection sensor;

wherein, when the driver's head is oriented such that the direction of breath is in the direction of the tracer gas detection sensor, the testing condition is satisfied; and wherein, when the driver's head is oriented such that direction of breath is not in the direction of the tracer gas detection sensor, the testing condition is not satisfied.

12. The method according to claim 1 wherein the tracer gas is CO2 and the analyte is ethyl alcohol (EtOH).

13. The method according to claim 12 wherein the concentration of the tracer gas is plotted as a function of time in order to determine the highest tracer gas concentration during a period of time, and further wherein the highest tracer gas concentration within the period of time corresponds to the peak in the tracer gas concentration.

14. The method according to claim 13 wherein a breath is determined to be present in the air in the interior of the vehicle when the peak in the tracer gas corresponds to a concentration between 400 ppm and 600 ppm.

15. The method according to claim 5 wherein the testing condition comprises the ON/OFF status of an HVAC system inside the vehicle, and further wherein when the HVAC system is set to the ON status, the testing condition is determined not to be within predetermined parameters.

16. The method according to claim 5 wherein the testing condition comprises the presence of windshield fluid, and further wherein when windshield fluid is detected, the testing condition is determined not to be within predetermined parameters.

17. The method according to claim 1 wherein the confidence interval is classified as "high confidence", "intermediate confidence" or "low confidence", and further wherein the classification of the confidence interval is a function of the number of peaks in the concentration of the tracer gas over a predetermined period of time, wherein a greater number of peaks in the concentration of the tracer gas during the predetermined period of time results in a classification of "high confidence", and a lower number of peaks in the concentration of the tracer gas results in a classification of "intermediate confidence" or "low confidence".

18. The method according to claim 5 wherein if, after initiation of the sensors to monitor the testing conditions, the predetermined time has elapsed without detecting a peak in the tracer gas and without determining that the testing conditions are within predetermined parameters, requiring the driver to provide an active breath sample.

19. The method according to claim 1 wherein the signal provided to the vehicle is denoted as "Low" if the concentration of the analyte does not exceed a predetermined set point, and further wherein the "Low" signal permits the vehicle to be operated.

20. The method according to claim 1 wherein the signal provided to the vehicle is denoted as "High" if the concentration of the analyte exceeds a predetermined set point, and further wherein the "High" signal disables operation of the vehicle.

21. The method according to claim 1 wherein the signal provided to the vehicle is denoted as "Intermediate" if the concentration of the analyte exceeds a predetermined lower boundary point and does not exceed a predetermined upper boundary point.

22. The method according to claim 1 wherein the peaks in the concentration of the tracer gas are determined by plotting the concentration of the tracer gas against time, and further wherein a peak in the tracer gas is characterized by a peak value having a concentration above 525 ppm and a duration of between 1-3 seconds.

23. The method according to claim 22 wherein each peak in the concentration of the tracer gas is characterized by a rise time and a decline time, wherein the rise time comprises the time that the concentration of the tracer gas rises from zero to the peak value, and wherein the decline time comprises the time that the concentration of the tracer gas declines from the peak value to zero.

24. The method according to claim 23 wherein the rise time is 0.5-1.0 seconds, and the decline time is 3.0-5.0 seconds.

25. The method according to claim 1 wherein, for N number of air samples, N number of signals representing the concentration of the tracer gas and the concentration of the analyte present in each of the N number of air samples are provided, and further comprising using an adder block to calculate the accumulated concentration of the analyte.

* * * * *